United States Patent [19]
Watanabe et al.

[11] Patent Number: 6,093,860
[45] Date of Patent: Jul. 25, 2000

[54] METHOD FOR PRODUCING PERFLUORO (N-PENTANE)

[75] Inventors: Kunio Watanabe; Takashi Okazoe; Shin Tatematsu, all of Yokohama, Japan

[73] Assignee: Asahi Glass Company Ltd., Tokyo, Japan

[21] Appl. No.: 09/337,395

[22] Filed: Jun. 22, 1999

[30] Foreign Application Priority Data

Jun. 24, 1998 [JP] Japan .................................. 10-177726

[51] Int. Cl.$^7$ .................................................. C07C 17/00
[52] U.S. Cl. ............................................ 570/175; 570/153
[58] Field of Search ..................................... 570/175, 153

[56] References Cited

U.S. PATENT DOCUMENTS

| | | |
|---|---|---|
| 3,917,726 | 11/1975 | von Halasz . |
| 4,510,335 | 4/1985 | Lagow et al. . |
| 4,754,085 | 6/1988 | Gervasutti et al. . |
| 5,093,432 | 3/1992 | Bierschenk et al. . |
| 5,162,594 | 11/1992 | Krespan .................................. 570/153 |
| 5,322,790 | 6/1994 | Scharp et al. . |
| 5,322,903 | 6/1994 | Bierschenk et al. . |
| 5,322,904 | 6/1994 | Bierschenk et al. . |
| 5,461,117 | 10/1995 | Bierschenk et al. . |
| 5,571,870 | 11/1996 | Bierschenk et al. . |
| 5,674,979 | 10/1997 | Schramm et al. . |
| 5,753,776 | 5/1998 | Bierschenk et al. . |

FOREIGN PATENT DOCUMENTS 0219823  4/1987  European Pat. Off. ............... 570/175

OTHER PUBLICATIONS

Patent Abstracts of Japan, vol. 097, No. 011, Nov. 28, 1997, JP 09 173773, Jul. 8, 1997 & Chemical Abstracts, vol. 127, No. 7, Aug. 18, 1997, Abstract No. 98975.

*Primary Examiner*—Alan Siegel
*Attorney, Agent, or Firm*—Oblon, Spivak, McClelland, Maier & Neustadt, P.C.

[57] ABSTRACT

A method for producing perfluoro(n-pentane), which comprises fluorinating perfluoro(2-pentene) by bringing the perfluoro(2-pentene) into contact with a fluorine gas in the presence of a solvent.

15 Claims, No Drawings

METHOD FOR PRODUCING PERFLUORO (N-PENTANE)

The present invention relates to a method for producing perfluoro(n-pentane) ($F(CF_2)_5F$, hereinafter referred to as "n-$C_5F_{12}$").

As a method for producing n-$C_5F_{12}$, there are known (1) a method for producing n-$C_5F_{12}$, together with $NF_3$, by electrolytic fluorination of dipiperidinomethane or the like (Hoffmann et al., J. Am. Chem. Soc., 79, 1957, 3424) and (2) a method for producing n-$C_5F_{12}$ by perfluorinating n-pentane in the presence of cobalt fluoride (Burford et al., Ind. Eng. Chem., 39, 1947, 328).

The above method (1) has various problems that an electric power consumed is high, that a selectivity of n-$C_5F_{12}$ is low and that a large amount of perfluoroisopentane which is an isomer having a boiling point close to that of n-$C_5F_{12}$ is by-produced. The by-production of this isomer raises a large problem when the product is used as a pharmaceutical.

The above method (2) has various problems that the reaction temperature is such a high temperature as from 150 to 300° C., thus requiring a special reaction apparatus, and that the reaction system contains such a heavy metal as cobalt. Therefore, when the product is used as a pharmaceutical, such a metal component as cobalt or the like in the product must be completely removed.

The present invention is to solve the above mentioned problems of the conventional methods, and provides a novel method for selectively producing highly pure n-$C_5F_{12}$ at a low expense without employing a special purification method.

That is, the present invention provides a method for producing n-$C_5F_{12}$, characterized by fluorinating perfluoro (2-pentene) ($CF_3CF=CFCF_2CF_3$, hereinafter referred to as "2-$C_5F_{10}$") by bringing the perfluoro(2-pentene) into contact with a fluorine gas in the presence of a solvent.

2-$C_5F_{10}$ used as a starting material in the present invention is a well known compound. 2-$C_5F_{10}$ can be prepared by subjecting tetrafluoroethylene ($CF_2=CF_2$) and hexafluoropropylene ($CF_3CF=CF_2$) to addition reaction in the presence of an aluminum-containing catalyst. The addition reaction is well known (U.S. Pat. No. 5,268,122), and can be carried out under well known conditions. This method produces the aimed product at a low expense and a high yield.

As the aluminum-containing catalyst, an aluminum-containing catalyst activated with fluorine or chlorine is preferable, and aluminum fluoride chloride (e.g. $AlCl_{3-x}F_x$, wherein x is a positive number of less than 3) and aluminium oxyfluoride chloride ($Al_2O_xF_yCl_z$, wherein each of x, y and z is a positive number and 2x+y+z=6) are particularly preferable. The catalyst can be prepared by reacting aluminium chloride with hydrogen fluoride, chlorofluorocarbons or fluorocarbons. Also, this reaction can be carried out usually in the absence of a solvent.

2-$C_5F_{10}$ has a cis-form and a trans-form, the steric configurations of a double bond of which are different 2-$C_5F_{10}$ used in the present invention may be in any form of a cis-form, a trans-form or a mixture of a cis-form and a trans-form, and any of these isomers can be satisfactorily reactive.

In the present invention, 2-$C_5F_{10}$ is fluorinated by being brought into contact with a fluorine gas in the presence of a solvent. An amount of the fluorine gas is preferably at least 2 times mols, more preferably from 2 to 10 times mols, to 2-$C_5F_{10}$. If the amount of the fluorine gas is too small, a dimerization reaction occurs and an amount of a by-product tends to become large.

In this step, it is preferable to supply 2-$C_5F_{10}$, together with a fluorine gas, into a solvent, thereby directly adding the fluorine gas to 2-$C_5F_{10}$. By this method, n-$C_5F_{12}$ is produced. n-$C_5F_{12}$ produced by the method of the present invention has a high purity and does not substantially contain an isomer, and therefore the method of the present invention is a method of high yield.

Examples of the solvent present in the reaction of 2-$C_5F_{10}$ and the fluorine gas in the method of the present invention, include a solvent inert to the fluorination reaction or a specific solvent active to the fluorination reaction.

A preferable example of the solvent inert to the fluorination reaction includes n-$C_5F_{12}$. Since n-$C_5F_{12}$ is the same compound as the aimed product, it is not necessary to carry out a purification step during the reaction and after the reaction. Also, examples of a solvent other than n-$C_5F_{12}$ include a fluorinated solvent which does not cause azeotropic boiling with n-$C_5F_{12}$ or chlorofluorocarbons, particular examples of which include perfluoropolyethers (tradename: KRYTOX, FOMBLIN, GALDEN, Demnum), per (fluorochloro)carbons (tradename: Flon Lube), tris (perfluoroalkyl)amine (tradename: Fluorinert), and the like.

Examples of the specific solvent active to the fluorination reaction include preferably a solvent which forms n-$C_5F_{12}$ by being fluorinated, particularly hydrofluoropentanes, more particularly decafluoro(n-pentane), undecafluoro(n-pentane), and the like.

The solvent efficiently removes reaction heat of the fluorination reaction, and is an essential component for preventing a carbon-carbon bond of a compound from disconnection in the reaction system. An amount of the solvent is preferably at least 5 times weight, more preferably from 5 to 10 times weight, to 2-$C_5F_{10}$. The presence of the solvent raises the selectivity of the reaction high.

The fluorine gas used in the reaction may be diluted with an inert gas such as nitrogen gas. The mixing ratio of the fluorine gas and the inert gas is not specially limited, but if the amount of the inert gas is too large, it becomes difficult to recover n-$C_5F_{12}$. Therefore, the fluorine gas concentration in the mixture gas is preferably at least 10%, more preferably at least 20%.

A reaction system of the fluorination reaction may be a batch system or a continuous system. This is more concretely illustrated hereinafter. Among the following systems, it is particularly preferable to employ a continuous system (No. 2) in view of reaction yield and selectivity.

(Batch system)

2-$C_5F_{10}$ or 2-$C_5F_{10}$ and a solvent are charged into a reactor, and stirring is initiated. When 2-$C_5F_{10}$ is charged, a fluorine gas and a solvent are supplied into the reactor until a predetermined pressure is obtained under a predetermined controlled temperature, and when 2-$C_5F_{10}$ and a solvent are charged, a fluorine gas or a fluorine gas and a solvent are supplied until a predetermined pressure is obtained under a predetermined controlled temperature. When the reduction of the pressure in the reactor is stopped, an inert gas in the system (if any) is purged, and a fluorine gas is supplied again until the predetermined pressure is obtained. The purging of the inert gas and the supplying of the fluorine gas are repeated until a predetermined amount of a fluorine gas is supplied.

(Continuous system No. 1)

2-$C_5F_{10}$ or 2-$C_5F_{10}$ and a solvent are charged into a reactor, and stirring is initiated. When 2-$C_5F_{10}$ is charged, a fluorine gas and a solvent are continuously supplied in a predetermined amount while controlling a reaction temperature and a reaction pressure to a predetermined level, and when 2-$C_5F_{10}$ and a solvent are charged, a fluorine gas or a fluorine gas and a solvent are continuously supplied in a predetermined amount while controlling a reaction temperature and a reaction pressure to a predetermined level.
(Continuous system No. 2)

A solvent is charged into a reactor, and stirring is initiated. 2-$C5F_{10}$ and a fluorine gas or 2-$C_5F_{10}$ and a solvent and a fluorine gas are continuously supplied in a predetermined molar ratio while controlling a reaction temperature and a reaction pressure to a predetermined level.

With regard to the above three methods, a supplying molar ratio of a fluorine gas and 2-$C_5F_{10}$ is illustrated below. That is, in the case of batch system, it is preferable to supply a fluorine gas in an excess amount, particularly at least two times mols, to an amount of 2-$C_5F_{10}$ charged. in the cases of continuous systems (No. 1 and No. 2), it is preferable to supply a fluorine gas constantly in an excess amount, particularly at least two times mols, to 2-$C_5F_{10}$ in view of selectivity.

Also, when supplying 2-$C_5F_{10}$ in the continuous system (No. 2), it is preferable to supply 2-$C_5F_{10}$ diluted with a solvent in order to improve selectivity and to prevent formation of a by-product. An amount of a solvent to dilute 2-$C_5F_{10}$ is preferably at least 5 times weight, particularly at least 10 times weight, to 2-$C_5F_{10}$.

A reaction temperature of the fluorination reaction is preferably from −100° C. to +100° C., more preferably from −50° C. to +50° C., most preferably from −20° C. to room temperature (about 25° C.) in view of reaction yield, selectivity and other industrial production conditions.

A reaction pressure of the fluorination reaction is not specially limited, but preferably from normal pressure to 0.5 MPa (absolute pressure, hereinafter the same) in view of reaction yield, selectivity and other industrial production conditions.

When 2-$C_5F_{10}$ remains in the product of the fluorination reaction, it is preferable to add a small amount of benzene or to carry out irradiation with ultraviolet light in the state of the presence of a fluorine gas at the latter stage of the fluorination reaction. An amount of benzene added is preferably from 0.1 to 5 mol % to 2-$C_5F_{10}$. Also, the irradiation time with ultraviolet light is preferably from 0.1 to 3 hours. This operation raises a conversion higher.

n-$C_5F_{12}$ which is the product of the method of the present invention is a useful compound used as a contrast medium for ultrasonic diagnosis.

EXAMPLES

Preparation Examples of 2-$C_5F_{10}$ (Examples 1 to 2), Examples of the present invention (Examples 3 to 17) and Comparative Example (Example 18) are illustrated hereinafter, but the present invention should not be limited thereto.

Example 1

682 g of hexafluoropropylene and 90 g of aluminium chloride fluoride catalyst fluorinated with trichlorofluoromethane were charged into a 2 l-nickel-made autoclave, and 463 g of tetrafluoroethylene was continuously supplied thereto while controlling a reaction temperature from −20 to +20° C. and controlling an internal pressure of the reactor to at most 0.5 MPa. Tetrafluoroethylene was supplied in an amount of 463 g in total. Further, a crude liquor obtained after the reaction was washed with water and distilled to obtain 720 g of 2-$C_5F_{10}$. A trans-form/cis-form ratio was 6.9/1.

Example 2

100 ml of γ-alumina of 3 mmφ was filled into an Inconel-made U letter type reactor, and the reactor was heated at 200° C. and was dried in a nitrogen atmosphere for 3 hours. Thereafter, nitrogen/dichlorodifluoromethane was passed in a volume ratio of 3/1 for 24 hours, and 100 g of aluminum oxychloride fluoride catalyst chlorinated and fluorinated was charged to react 228 g of hexafluoropropylene and 154 g of tetrafluoroethylene in the same manner as in Example 1. Further, a crude liquor obtained after the reaction was washed with water and distilled to obtain 240 g of 2-$C_5F_{10}$. A trans-form/cis-form ratio was 7.5/1.

Example 3

1 l of perfluorotributylamine (($C_4F_9$)$_3$N, hereinafter referred to as "PFTBA") as a solvent was charged into a 2 l-nickel-made autoclave, and 20% fluorine gas (dilution gas: nitrogen gas) was continuously supplied quantitatively into the solvent by a mass flow controller, and 2-$C_5F_{10}$ prepared in Example 1 or Example 2 was diluted with PFTBA (weight ratio: starting material/solvent=1/10) and was continuously supplied into the reactor. The fluorine gas was supplied in an excess amount (2 times mols) to 2-$C_5F_{10}$. A condenser cooled at −10° C. was provided at the outlet of the reactor. The reaction temperature was −10° C. and the reaction pressure was atmospheric pressure. A reaction crude liquor containing n-$C_5F_{12}$ was analyzed by gas chromatography, and the reaction results were a conversion of 96.6%, a selectivity of 86.9% and a recovery rate (percentage of mols of n-$C_5F_{12}$ actually recovered to mols of 2-$C_5F_{10}$ charged) of 81.9%. Also, perfluoroisopentane was not detected in a crude liquor obtained after the reaction, and the main by-product was $C_{10}F_{22}$.

Also, in any of the following Examples, perfluoroisopentane was not detected, and the main by-product was $C_{10}F_{22}$.

Example 4

The same procedure as in Example 3 was repeated, except that n-$C_5F_{12}$ was used as a solvent in place of PFTBA. The results were a conversion of 98.7% and a selectivity of 91.4%.

Example 5

The same procedure as in Example 3 was repeated, except that n-$C_5F_{12}$ was used as a solvent in place of PFTBA and 2-$C_5F_{10}$ was supplied without being diluted with a solvent. The results were a conversion of 98.5% and a selectivity of 65.3%.

Example 6

The same procedure as in Example 3 was repeated, except that 1,1,1,2,3,4,4,5,5,5-decafluoro(n-pentane) ($CF_3CHFCHFCF_2CF_3$, hereinafter referred to as "$C_5H_2F_{10}$") was used as a solvent and 2-$C_5F_{10}$ was supplied without being diluted with a solvent. The results obtained after subtracting amounts of undecafluoro(n-pentane) and n-$C_5F_{12}$ produced from $C_5H_2F_{10}$, were a conversion of 94.9% and a selectivity of 83.7%.

Examples 7 to 15

Examples 7 to 15 were carried out in the same manner as in Example 3, except that the fluorine gas concentration (20%), the reaction temperature (−10° C.) and the reaction pressure (atmospheric pressure) used in Example 3 were respectively changed as shown in the following Table 1. The results are shown in the following Table 1.

TABLE 1

|  |  | Conversion | Selectivity | Recovery rate |
|---|---|---|---|---|
| Example 7 | Fluorine concentration 5% | 95.7% | 82.3% | 70.8% |
| Example 8 | Fluorine concentration 10% | 97.1% | 84.0% | 74.6% |
| Example 9 | Fluorine concentration 40% | 98.1% | 85.2% | 81.6% |
| Example 10 | Reaction temperature −30° C. | 93.0% | 85.1% | |
| Example 11 | Reaction temperature −20° C. | 96.4% | 86.7% | |
| Example 12 | Reaction temperature 0° C. | 97.5% | 86.4% | |
| Example 13 | Reaction temperature 25° C. | 98.7% | 85.2% | |
| Example 14 | Reaction pressure 0.2 MPa | 98.0% | 86.4% | |
| Example 15 | Reaction pressure 0.5 MPa | 98.1% | 86.2% | |

Example 16

3 mol % of benzene was added to 2-$C_5F_{10}$ remaining in the crude liquor obtained after the reaction of Example 3.

Further, a fluorine gas was blown in an amount of 2 times mols into 2-$C_5F_{10}$ remaining in the reaction crude liquor, and the mixture was maintained for 1 hour. The reaction crude liquor thus obtained was analyzed, and a conversion and a selectivity were determined from the total amount of 2-$C_5F_{10}$ supplied and a total amount of n-$C_5F_{12}$ produced. The results were a conversion of 99.5% and a selectivity of 86.4%.

Example 17

The reaction crude liquor of Example 3 was placed in a stirring tank made of PFA resin (tetrafluoroethylene/perfluoro(alkylvinyl ether) copolymer), and was cooled to −20° C., and 20% fluorine gas (dilution gas: nitrogen) was supplied by a mass flow controller under irradiation with a high pressure mercury lamp, and the content was stirred for 1 hour. An amount of the fluorine gas supplied was 2 times mols to 2-$C_5F_{10}$ remaining in the reaction crude liquor. The reaction crude liquor thus obtained was analyzed, and the results were a conversion of 99.9% and a selectivity of 86.9%.

Example 18

A 1 l-U letter type flowing reactor (outer diameter 2.54 cm) made of Inconel 600 was dipped in a thermostat maintained at 30° C., and 2-$C_5F_{10}$ was supplied in an amount of 0.06 mol per hour and 20% fluorine gas (dilution gas: nitrogen) was supplied in an amount of 0.12 mol per hour by a mass flow controller thereto, and a gas phase reaction was carried out in the absence of a solvent. As a result, a conversion was 99.7% and a selectivity was 10.2%. The main by-product in the reaction product was $C_{1-4}$ perfluorohydrocarbons.

According to the present invention, the aimed n-$C_5F_{12}$ was produced at a high selectivity and a high conversion in a simple production apparatus by a simple operation, as compared with the conventional methods. Since the n-$C_5F_{12}$ obtained by this method does not contain such an isomer as to be hardly removable, purification operation can be carried out in a simple manner. Also, when n-$C_5F_{12}$ is used as a pharmaceutical intermediate or pharmaceutical, the method of the present invention is advantageous since the product is highly pure and extra impurities are not incorporated in the final product.

What is claimed is:

1. A method for producing perfluoro(n-pentane), which comprises fluorinating perfluoro(2-pentene) by bringing the perfluoro(2-pentene) into contact with a fluorine gas in the presence of a solvent, wherein said fluorine gas is maintained in an amount of at least 2 moles of fluorine per mole of perfluoro(2-pentene).

2. A method for producing perfluoro(n-pentane), which comprises subjecting tetrafluoroethylene and hexafluoropropylene to addition reaction in the presence of an aluminum-containing catalyst to form perfluoro(2-pentene), and then bringing the perfluoro(2-pentene) into contact with a fluorine gas in the presence of a solvent, wherein said fluorine gas is maintained in an amount of at least 2 moles of fluorine per mole of perfluoro(2-pentene).

3. The method according to claim 1, wherein the fluorine gas is used in an amount of at least two times mols to the perfluoro(2-pentene).

4. The method according to claim 2, wherein the fluorine gas is used in an amount of at least two times mols to the perfluoro(2-pentene).

5. The method according to claim 1, wherein the solvent is hydrofluoropentanes or a fluorinated solvent containing no hydrogen atom.

6. The method according to claim 2, wherein the solvent is hydrofluoropentanes or a fluorinated solvent containing no hydrogen atom.

7. The method according to claim 1, wherein the solvent is perfluoro(n-pentane) or hydrofluoropentanes convertible into perfluoro(n-pentane) by fluorination.

8. The method according to claim 2, wherein the solvent is perfluoro(n-pentane) or hydrofluoropentanes convertible into perfluoro(n-pentane) by fluorination.

9. The method according to claim 1, wherein the solvent is used in an amount of at least 5 times weight to the perfluoro(2-pentene).

10. The method according to claim 2, wherein the solvent is used in an amount of at least 5 times weight to the perfluoro(2-pentene).

11. The method according to claim 1, wherein a reaction temperature of the fluorination reaction is from −100° C. to +100° C.

12. The method according to claim 2, wherein a reaction temperature of the fluorination reaction is from −100° C. to +100° C.

13. The method according to claim 1, wherein the reaction is carried out by continuously supplying a fluorine gas and perfluoro(2-pentene) into a reaction system containing a solvent.

14. The method according to claim 2, wherein the reaction is carried out by continuously supplying a fluorine gas and perfluoro(2-pentene) into a reaction system containing a solvent.

15. The method according to claim 1, wherein the fluorine gas is maintained in an amount of from 2 to 10 moles of fluorine per mole of the perfluoro (2-pentene).

* * * * *